United States Patent
Sutton

(10) Patent No.: US 10,234,439 B2
(45) Date of Patent: Mar. 19, 2019

(54) METHODS AND SYSTEMS FOR ANALYZING A FIELD

(71) Applicant: Brian Harold Sutton, Lowell, IN (US)

(72) Inventor: Brian Harold Sutton, Lowell, IN (US)

(73) Assignee: Airscout Inc., Downingtown, PA (US)

( * ) Notice: Subject to any disclaimer, the term of this patent is extended or adjusted under 35 U.S.C. 154(b) by 330 days.

(21) Appl. No.: 15/005,612

(22) Filed: Jan. 25, 2016

(65) Prior Publication Data

US 2016/0216245 A1 Jul. 28, 2016

Related U.S. Application Data

(60) Provisional application No. 62/107,120, filed on Jan. 23, 2015.

(51) Int. Cl.
| | | |
|---|---|---|
| *G01N 33/00* | (2006.01) | |
| *G06T 7/00* | (2017.01) | |
| *G06K 9/00* | (2006.01) | |

(52) U.S. Cl.
CPC ..... *G01N 33/0098* (2013.01); *G06K 9/00657* (2013.01); *G06K 9/00664* (2013.01); *G06T 7/0016* (2013.01); *G06K 2209/17* (2013.01); *G06T 2207/10024* (2013.01); *G06T 2207/10032* (2013.01); *G06T 2207/10048* (2013.01); *G06T 2207/30188* (2013.01)

(58) Field of Classification Search
CPC ........... G01N 33/0098; G06K 9/00657; G06K 9/00664; G06K 2209/17; G06T 7/0016; G06T 2207/10024; G06T 2207/10032; G06T 2207/10048; G06T 2207/30188
See application file for complete search history.

(56) References Cited

U.S. PATENT DOCUMENTS

| | | |
|---|---|---|
| 5,453,618 A | 9/1995 | Sutton |
| 5,467,271 A | 11/1995 | Abel et al. |
| 5,764,819 A * | 6/1998 | Orr .......................... A01G 7/00 348/144 |
| 5,878,356 A | 3/1999 | Garrot, Jr. et al. |
| 6,212,824 B1 | 4/2001 | Orr et al. |
| 6,597,991 B1 | 7/2003 | Meron et al. |
| 7,058,197 B1 | 6/2006 | McGuire et al. |
| 7,184,859 B2 | 2/2007 | Hood et al. |
| 7,194,111 B1 | 3/2007 | Schaum et al. |
| 7,715,013 B2 | 5/2010 | Glaser et al. |
| 8,194,916 B2 | 6/2012 | Ma |
| 9,354,216 B2 * | 5/2016 | Sutton ................ G01N 33/0098 |
| 2004/0005085 A1 * | 1/2004 | Andersen ............ G08B 17/005 382/109 |
| 2005/0149235 A1 | 7/2005 | Seal et al. |
| 2008/0112029 A1 | 5/2008 | Bodkin |

(Continued)

OTHER PUBLICATIONS

International Search Report and Written Opinion, PCT/US16/38877, Report dated Oct. 18, 2016.

*Primary Examiner* — Jonathan Dunlap
*Assistant Examiner* — Philip Cotey
(74) *Attorney, Agent, or Firm* — Hartman Global IP Law; Gary M. Hartman; Domenica N. S. Hartman

(57) ABSTRACT

A method and system for monitoring the health and growth of plants in a field. The method and system acquire a thermal image indicative of thermal energy emitted by the plants and process the thermal image to assess variations in the temperatures among the plants.

20 Claims, 12 Drawing Sheets

(56) References Cited

U.S. PATENT DOCUMENTS

| | | |
|---|---|---|
| 2008/0308732 A1 | 12/2008 | Warnke et al. |
| 2009/0321644 A1 | 12/2009 | Vogt et al. |
| 2011/0047867 A1* | 3/2011 | Holland .................... G01J 3/10 47/1.5 |
| 2012/0155714 A1* | 6/2012 | Douglass ........... G06K 9/00657 382/110 |
| 2012/0288159 A1* | 11/2012 | Asner ................ G06K 9/00657 382/110 |
| 2013/0114641 A1 | 5/2013 | Sutton |
| 2013/0325346 A1 | 12/2013 | McPeek |
| 2014/0098238 A1 | 4/2014 | Boulanger et al. |
| 2014/0168412 A1 | 6/2014 | Shulman et al. |
| 2015/0193917 A1* | 7/2015 | Schachter ................ H04N 5/33 348/113 |
| 2018/0267008 A1* | 9/2018 | Sutton ................ G01N 33/246 |

* cited by examiner

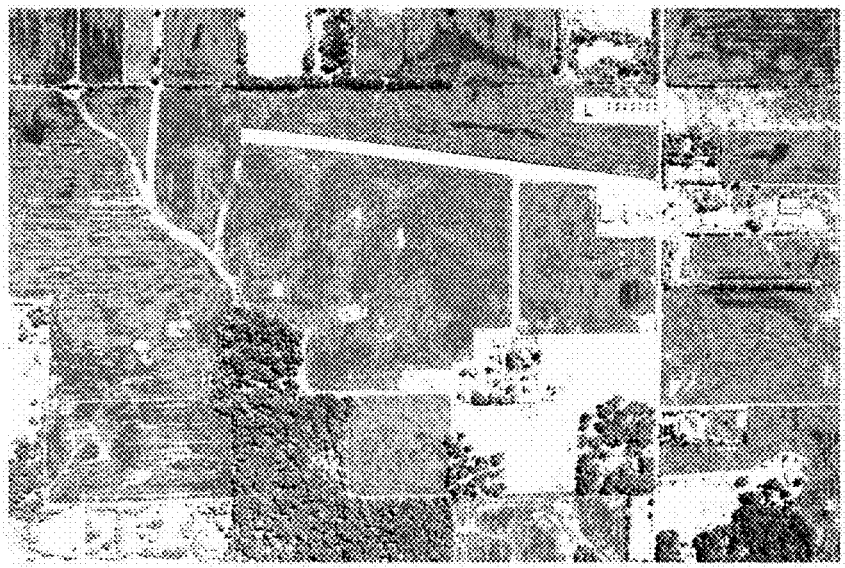
FIG. 6

METHODS AND SYSTEMS FOR ANALYZING A FIELD

CROSS REFERENCE TO RELATED APPLICATIONS

This application claims the benefit of U.S. Provisional Application No. 62/107,120, filed Jan. 23, 2015, the contents of which are incorporated herein by reference. In addition, this application is related to co-pending U.S. patent application Ser. No. 13/670,897, filed Nov. 7, 2012, the contents of which are incorporated herein by reference.

BACKGROUND OF THE INVENTION

The present invention generally relates to methods of monitoring the health and growth of plants. More particularly, this invention relates to aerial imaging of vegetation to determine, monitor, and predict plant health and growth.

Various technologies have been used in the past to measure temperature of plant leaves. For example, U.S. Pat. No. 7,058,197 uses visual light reflectance to generate NDVI (normalized difference vegetation index) images. This patent relies on reflected light from the sun, and therefore teaches that the optimum time for image acquisition using the disclosed process is within two hours of "solar noon" and on cloudless days. This makes it very impractical for a commercial application. In particular, this patent discloses > Aerial imagery was collected four times throughout the growing season. The image dates correlated with bare soil, VI2, VT, and R4 crop stages (see section on "Resolutions in Remote Sensing"). The aerial imagery was flown with digital cameras with an array size of approximately 1500 pixels wide and 1000 pixels in the along track dimension. The digital systems were 8-bit systems and were collected and stored on an on-board computer in a Tagged Image Format (TIF). Four bands were collected representing the blue, green, red, and near infrared portions of the electromagnetic spectrum (see section on "Spectral Nature of Remote Sensing"). The cameras were aligned in a two-by-two matrix and were rigid mounted (pseudo-bore sited) with the lenses focussed [sic] on infinity. The imagery was flown at approximately 5000 feet above ground level (AGL) to produce a spatial resolution of approximately one meter by one meter (see section on "Resolutions in Remote Sensing"). The digital cameras have square pixels and are not interlaced during image acquisition. The optimum time for image acquisition was two hours before or two hours after solar noon (see section on "Resolutions in Remote Sensing"). Images were not acquired during times of poor atmospheric conditions (haze, rain, clouds). No cloud shadows were acceptable in the imagery.

In addition, it appears that the methodology disclosed by U.S. Pat. No. 7,058,197 is only able to indicate that a problem exists after a plant has actually changed its structure, as indicated by its color. In many cases, this is too late to take corrective action. Column 6 of U.S. Pat. No. 7,058,197 describes the extent of the methodology's capability as follows:

> The third major division of the electromagnetic spectrum ranges from around 1500 nanometers to approximately 3000 nanometers and is referred to as the middle-infrared. It is this portion of the electromagnetic spectrum where moisture plays a dominant role. Although other factors such as organic matter, iron content, and clay content have an effect, moisture appears be the primary mechanism affecting reflectance. More specifically, the higher the moisture content, the lower the reflectance. As objects lose moisture or begin to dry, their reflectance in this portion of the electromagnetic spectrum increases. While this concept has been proven in a laboratory setting, applying this concept in practice has been somewhat evasive.

As another example, U.S. Pat. No. 6,597,991 uses thermal imaging to detect water content in leaves for irrigation purposes. This patent is reliant on obtaining actual temperatures and using ground-based references for calibration. Arguably, a significant disadvantage of U.S. Pat. No. 6,597,991 is its reliance on extremely accurate temperature measurements so that the need for irrigation can be determined. Such a requirement necessitates an extra step and additional costs associated with the calibration. U.S. Pat. No. 6,597,991 does not appear to contain a reference to the detection of disease in very early stages.

U.S. Pat. No. 6,212,824 uses various remote sensing and image analysis technologies for classifying plants in small fields. In particular, this patent discloses > The present invention employs remote sensing technology to classify inbred and hybrid plants and segregating populations for commercially important traits such as yield, environmental stress responses, disease resistance, insect and herbicide resistance, and drought resistance. Images are prepared from remote sensing data obtained from plants.
>
> These evaluations are useful in decision making to select plants from early generations or preliminary tests used in breeding, to be advanced for selective breeding.

U.S. Pat. No. 6,212,824 discloses the use of both thermal imaging and reflectance at various wavelengths (multiple bands) for imaging vegetation from an aircraft in order to classify plants. However, it does not appear that the patent uses long-wave thermal images of a type capable of use for monitoring the growth of vegetation, predicting future growth of vegetation, and/or detecting disease, insect infestation, or other stress factors in vegetation before they become apparent to visual or near-infrared cameras. Rather the patent appears to focus on visual and near-infrared wavelengths. For example, the patent states > In an exemplary embodiment, CIR photographs revealed qualitative differences between the four row subplots across both limited and full irrigation treatments (FIG. 4). These photographs were subsequently processed (FIG. 5) to generate quantified values for the three bands or wavelengths of reflectance used to create the photograph. The three bands 20 were green, red and near-infrared (not thermal) portions of the energy spectrum. FIGS. 6-8 show the green, red and near-infrared results on the same field as in FIG. 4. The red and near-infrared bands were considered to be indications of the crop conditions, having been used by others in crop assessment programs. The red band corresponds to chlorophyll absorption and, according to theory, reflectance in this band increases during times of stress. Reflectance in the near-infrared region is predicted to decrease with increasing stress. The near-infrared region is believed to be related to plant structure and composition.

In view of the above, it can be appreciated that there are certain problems, shortcomings or disadvantages associated with the prior art, and that it would be desirable if an improved method were available for aerial monitoring of plant health and growth that does not rely solely on sensing reflected visible light and/or ground-based measurements.

BRIEF DESCRIPTION OF THE INVENTION

The present invention provides a method and system suitable for aerial imaging of vegetation to determine, monitor, and predict plant health and growth that does not rely solely on sensing reflected visible light and/or ground-based measurements.

According to one aspect of the invention, a method of monitoring plants in a field includes positioning a thermal imaging device in an aircraft, acquiring an aerial thermal image indicative of thermal energy emitted by the plants, and processing the thermal image to assess variations in the temperatures among the plants.

According to another aspect of the invention, a system for monitoring plants in a field includes means for acquiring an aerial thermal image indicative of thermal energy emitted by the plants with an aircraft while the aircraft is in flight and means for processing the thermal image to assess variations in the temperatures among the plants.

A technical effect of acquiring and processing the thermal image is the ability to monitor plant health and growth with aerial imaging at any time without the need for ground-based measurements. In particular, it is believed that, by acquiring a thermal image indicative of thermal energy emitted by the plants and processing the thermal image to assess variations in the temperatures among the plants, a trained thermographer or computer software can monitor the growth of vegetation, predict future growth of vegetation, and/or detect disease, insect infestation, or other stress factors in vegetation before they become apparent to visual or near-infrared cameras.

Another aspect of the invention is assessing the variations in temperatures among the plants in order to detect disease in the plants, detect insect infestation in the plants, and/or to predict a future yield of the plants.

Another aspect of the invention is acquiring a digital visual image of at least a portion of a field that is indicative of light reflected by plants within the portion while the aircraft is in flight, the visual image capturing light in the near-infrared, visual, and ultraviolet spectrums, and processing the visual image to assess relative variations in light reflectance among the plants.

A technical effect of acquiring and processing the digital visual image is the ability to monitor plant health and growth with aerial imaging. In particular, it is believed that, by acquiring a digital visual image indicative of light reflected by plants and processing the visual image to assess relative variations in light reflectance among the plants, stress factors such as a lack of nutrients may be determined and used to build prescription maps for seed and fertilizer for individual fields, and to apply rescue treatments during the current season. The imagery may also be used to plan or adjust the planting and fertilizing for the following season.

Other aspects and advantages of this invention will be better appreciated from the following detailed description.

BRIEF DESCRIPTION OF THE DRAWINGS

FIG. 6 includes an image of a field before and after analyzing the image to identify differences in color across the canopy of a crop in the field.

DETAILED DESCRIPTION OF THE INVENTION

Figure 1:
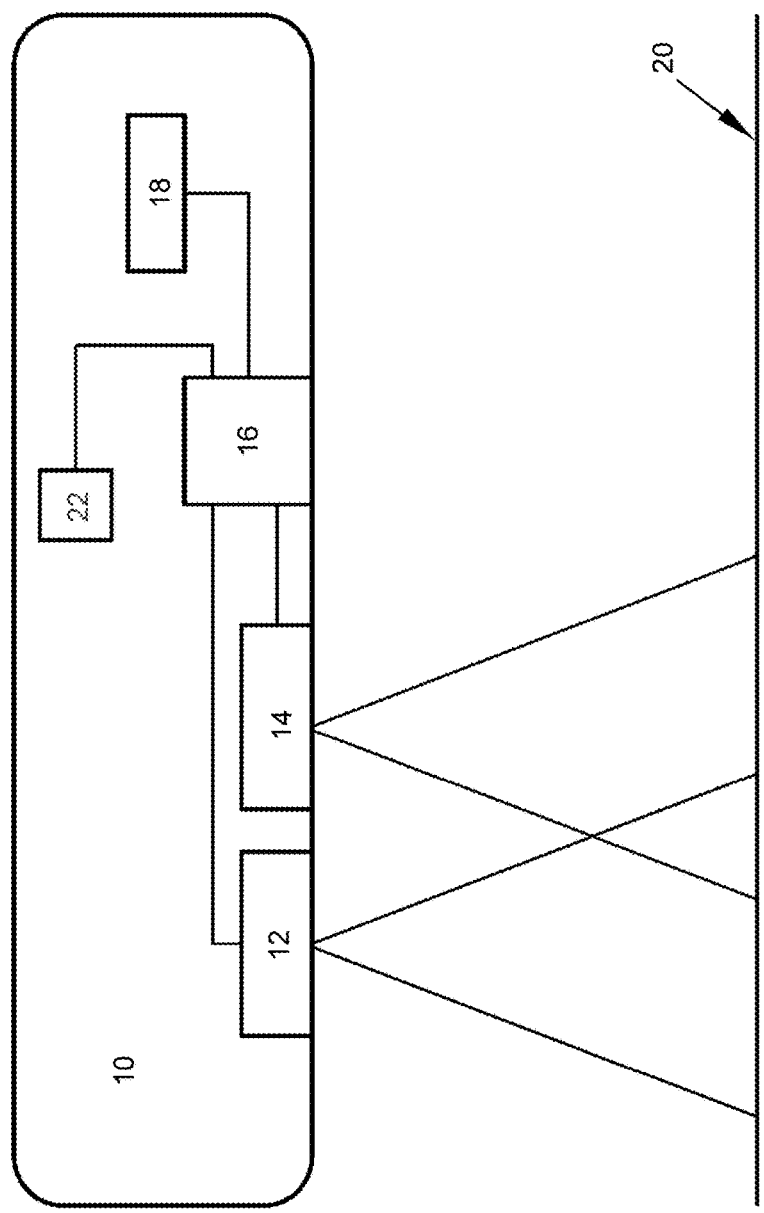
FIG. 1 is a schematic plan representing an imaging system in accordance with an aspect of this invention.

The present invention is generally applicable to imaging of plants utilizing energy (heat) emitted thereby and/or broad spectrum light reflected thereby. A particular aspect of the invention is based on a determination that by using certain microbolometer technology in a thermal imaging device, a trained thermographer or computer software can monitor the growth of vegetation, predict future growth of vegetation, and/or detect disease, insect infestation, or other stress factors in vegetation before they become apparent to visual or near-infrared cameras. While the invention is described as being suitable for monitoring plant health and growth, other applications are foreseeable and therefore the present invention should not be limited to the described embodiments herein. For example, an aspect of the invention includes predicting a future yield of a crop based on thermal images. The nonlimiting aspects of the invention described hereinafter are in reference to obtaining information about a field by imaging at least a portion of the field while an aircraft 10 is in flight over the field as represented in FIG. 1, preferably at an altitude of at least 5000 feet (about 1500 m) above ground level over the field being imaged. While it is foreseeable and within the scope of the invention that certain aspects of the invention may be used at lower altitudes, a minimum altitude is preferred such that entire fields may be viewed and relative differences over areas of the fields may be comparatively analyzed.

While not wishing to be held to any one theory, investigations leading to certain aspects of the present invention regarding disease detection in plants indicated that during the day, sick plants tend to be at an increased temperature relative to healthy plants due to a lack of evapotranspiration. These sick plants are represented in thermal images as being warmer than other healthier plants in the field. In contrast, during the night sick plants tend to be at a decreased temperature relative to healthier plants primarily since the healthier plants retain water comprising latent heat. Therefore, at night sick plants are represented in thermal images as being cooler than healthier plants in the field. The difference in temperature between the healthier plants and the sick plants will be dependent, at least in part, on the progression of the disease in the sick plants. Preferably, systems as described herein are capable of detecting variations in temperature that are relatively small and indicative of disease in a plant at a time in the progression of the disease prior to the disease being detectible to visual or near-infrared inspection.

Preferred embodiments of the invention employ a system comprising one or more high-resolution long-wave thermal imaging cameras 12 that preferably can be mounted in the aircraft 10, as schematically represented in FIG. 1, optionally along with a digital camera 14, for example, a twenty-one megapixel digital camera, that can be used to provide a digital image for reference purposes. While the thermal imaging camera 12 and the digital camera 14 may be mounted to the aircraft 10 by any means, preferably the thermal imaging camera 12 and the digital camera 14 are mounted in a baggage compartment of the aircraft 10 and exposed through several holes in the aircraft skin beneath the baggage compartment in accordance with FAA AC43.13. Computer equipment 16 for controlling the thermal imaging camera 12 and the digital camera 14 may be located in the cockpit including a monitor 18 for the purpose of displaying and monitoring the thermal and/or digital camera images. However, alternative locations for the thermal imaging camera 12, the digital camera 14, and computer equipment 16 are foreseeable.

A particular by nonlimiting example of a thermal imaging camera 12 that has been employed with the invention is manufactured by Infrared Cameras, Inc., of Beaumont, Tex. USA. The particular model of this thermal imaging camera is ICI 7640, equipped with a specially made 15 mm lens. The thermal imaging camera 12 produced an array of 480×640 pixels (currently considered to be high resolution, compared to thermal imaging cameras that offer resolutions of, for example, 320×240 pixels and 160×120 pixels) and used a microbolometer sensor that changes temperature as a result of being exposed to infrared (IR) energy (wavelengths between 0.7 and 300 micrometers). Images with resolutions lower than 480×640 pixels were found to be blurred when taken from high altitudes (e.g., at least 5000 feet above ground level over a field being imaged). Microbolometer sensors are considered to be "long wave" sensors because they collect light in wavelengths much longer than visible light, i.e., above the 0.4 to 0.7 micrometer spectral band. Wavelengths above visible light provide better penetration through smoke, smog, dust, and other interference that may be present under poor atmospheric conditions.

Suitable microbolometer sensors preferably collect light in wavelengths of between about 7 and 14 micrometers. The microbolometer sensor that was utilized with the ICI 7640 camera is especially sensitive to thermal energy (infrared radiation) and was capable of sensing wavelengths as long as 14 micrometers and as short as 7 micrometers or below. Wavelengths below 8 micrometers were found to be especially important for identifying disease in plants. During investigations leading to the present invention, it was determined that the size of the captured wavelength ranges influenced the results obtained. For example, wider captured wavelength ranges (for example, 7-14 micrometers) provided improved measurements for relative temperatures between plants but reduced accuracy of specific temperature measurements of individual plants. In contrast, narrower captured wavelength ranges (for example, 8-13 micrometers) provided improved accuracy of specific temperature measurements of individual plants but reduced measurements for relative temperatures between plants. It was further determined that measuring relative temperatures between plants in the field was critical to detecting and predicting disease, insect infestation, or other stress factors in the plants. Consequently, the microbolometer sensor is preferably capable of sensing wavelengths below 8 micrometers, and more preferably at or below 7 micrometers, and preferably simultaneously capable of sensing wavelengths above 13 micrometers, and more preferably at or above 14 micrometers. Equipped with its sensor, the thermal imaging cameras 12 preferably utilized by the invention do not require reflected light from the sun, and therefore allow the system and method of this invention to be used under poor atmospheric conditions (haze, rain, clouds, etc.), and even in the darkness of night.

In contrast, U.S. Pat. No. 7,058,197 uses digital cameras that work primarily with reflected light in wavelengths of 0.38 to 0.72 micrometer to see plant color. These wavelengths are in the visible spectrum and require a light source from something above 6000° C., such as a light bulb filament or the sun. The white light from this energy source then bounces back (reflects) off objects in different wavelengths, enabling colors to be seen. Consequently, U.S. Pat. No. 7,058,197 teaches that the optimum time for image acquisition is two hours before or two hours after solar noon. In contrast, suitable cameras for use with the present invention do not require a source of high energy because they measure energy that is emitted, not reflected, by plants.

U.S. Pat. No. 6,212,824 uses visual wavelengths in the 0.4 to 0.7 micrometer range and near-infrared wavelengths in the 0.7 to 1.1 micrometer range. These ranges are well outside the 7 to 14 micrometer wavelength range that is believed to be necessary for monitoring the growth of vegetation, predicting future growth of vegetation, and/or detecting disease, insect infestation, or other stress factors in vegetation in accordance with aspects of the present invention.

Because thermal imaging cameras believed to be suitable for use with this invention detect energy waves of much longer wavelengths, (e.g., 7 to 14 micrometers), the thermal imaging camera 12 is able to detect objects over a range of temperatures, for example, about −35° C. to about 200° C. A computer program can be used to focus the thermal imaging camera's sensitivity onto an area that encompasses a range of temperatures above and below the ambient temperature of the crop canopy, for example, about 10° C. above and below. A color palette can then be used in the computer program to build an image showing the relative temperature of the canopy. Such a computer program is well within the capabilities of those skilled in the relevant art, and therefore will not be discussed in any detail here.

In the above manner, certain aspects of the invention can be performed to evaluate plants under poor atmospheric conditions and even in total darkness and measure plant health and growth based on temperature, without the need for using reflected light as proposed by U.S. Pat. No. 7,058,197. A system as described herein can employ a technique by which the computer program is written to be further able to compensate for clouds if the images are taken during daylight hours. This can be accomplished by utilizing the aforementioned separate digital camera 14, whose digital images can overlay thermal images acquired with the thermal imaging camera 12. Since clouds are readily apparent in the visual digital image of the digital camera 14, the computer program can be used to compensate for cooler areas that exist beneath clouds. For this purpose, both thermal and visual digital images are preferably acquired of the field of interest simultaneously. The computer program may then analyze the visual digital image to recognize which portions of the image were under cloud cover, and then may adjust the corresponding portions in the thermal image to compensate for the cloud coverage. Similar methods may be used to compensate for other interfering elements such as wind.

At the time of the invention, thermal imaging cameras 12 of the type used by the invention were believed to be limited to one camera mounted on NASA's Space Shuttle and another leased to the University of Washington for environmental research. Up until the time of the invention, it was believed that there were no uncooled microbolometer thermal imaging cameras 12 commercially available with resolutions suitable for use with the present invention. This camera technology was previously developed for the U.S. military as the heat-seeking element in missile guidance systems, and has recently been made available to the general public. While thermal imaging cameras have been available for many years prior to the time of the invention, they were required to be cooled with liquid nitrogen and therefor impractical for use in most aircraft for safety and economic reasons.

Figure 8:
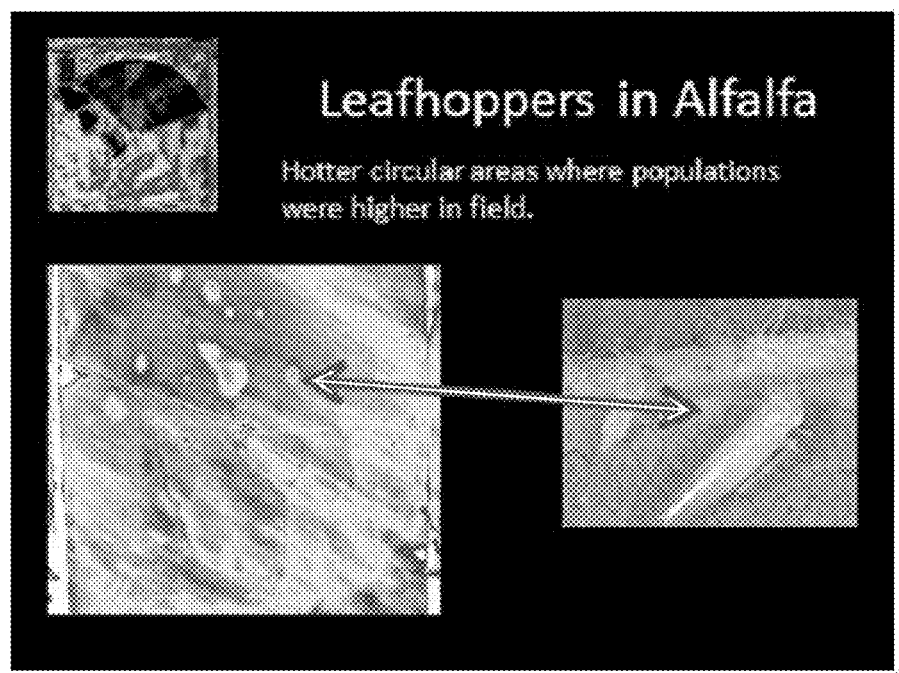
FIGS. 8-10 represent thermal and visual images corresponding to insect infestation (FIG. 8) and disease (FIGS. 9 and 10) in vegetation in a field.
Figure 9:
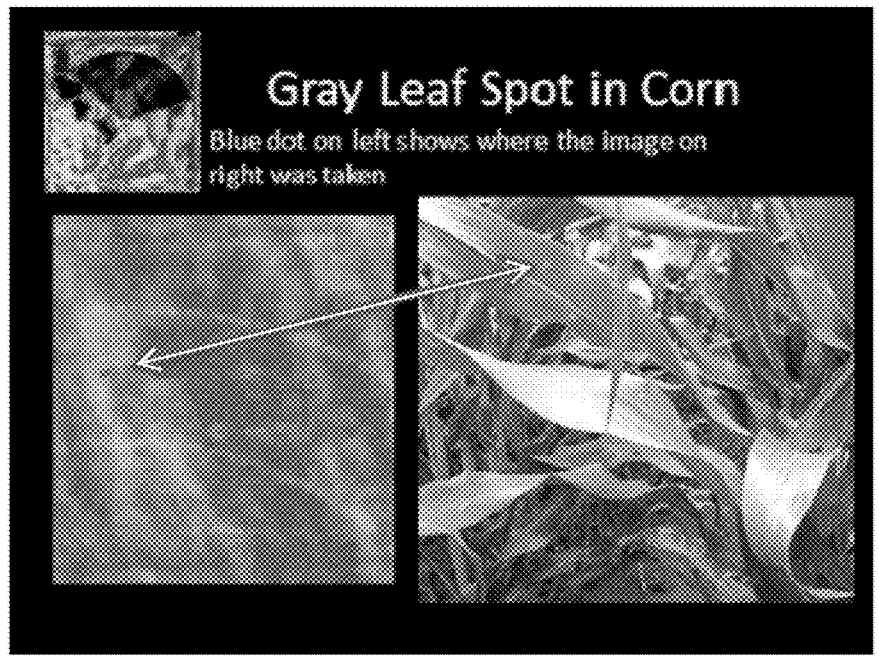
Figure 10:

Through the use of thermal imaging cameras of the types described above—and analytical software, a trained thermographer or software program can identify very subtle relative differences in canopy temperature. In fact, the thermal imaging camera manufactured by Infrared Cameras, Inc., as modified herein is capable of measuring differences of as little as 0.03° C. Through careful analysis of the thermal images, these subtle differences in temperature can guide a user on the ground to suspect areas in a field. For example, analysis of the thermal images may reveal patterns that stand out from those normally observed in healthy plants and may be related to patches of diseased or insect infested plants. FIGS. 8 through 10 represent exemplary thermal images comprising insect infestation and/or disease in vegetation in a field as well as visual images of the afflicted vegetation identified in the thermal images. In particular, FIG. 8 represents a thermal image of a field of alfalfa comprising a region where crops infested with pests (leafhoppers/Cicadellidae) were found, FIG. 9 represents a thermal image of a field of corn comprising a region where diseased (gray leaf spot) crops were found, and FIG. 10 represents a thermal image of a field of soybeans comprising a region where diseased (white mold) crops were found. Preferably, the system includes a computer software program capable of identifying patterns in the thermal images indicative of diseased plants. In order to detect disease or other ailments in time to treat the condition, and in particular detect such ailments at a time in the progression of the ailment prior to the ailment being detectible to visual or near-infrared inspection, the thermal imaging camera 12 preferably is extremely sensitive to relative temperatures between individual objects. Preferably, the thermal imaging camera's sensitivity, generally measured by a parameter referred to as noise equivalent temperature difference (NETD), is at least 0.03° C. or lower at optimum ambient temperatures. Less sensitive cameras have been found to be incapable of properly identifying differences in temperature necessary for early detection of disease in vegetation in fields imaged from high altitudes (i.e., greater than 5000 feet above ground level).

Figure 7:
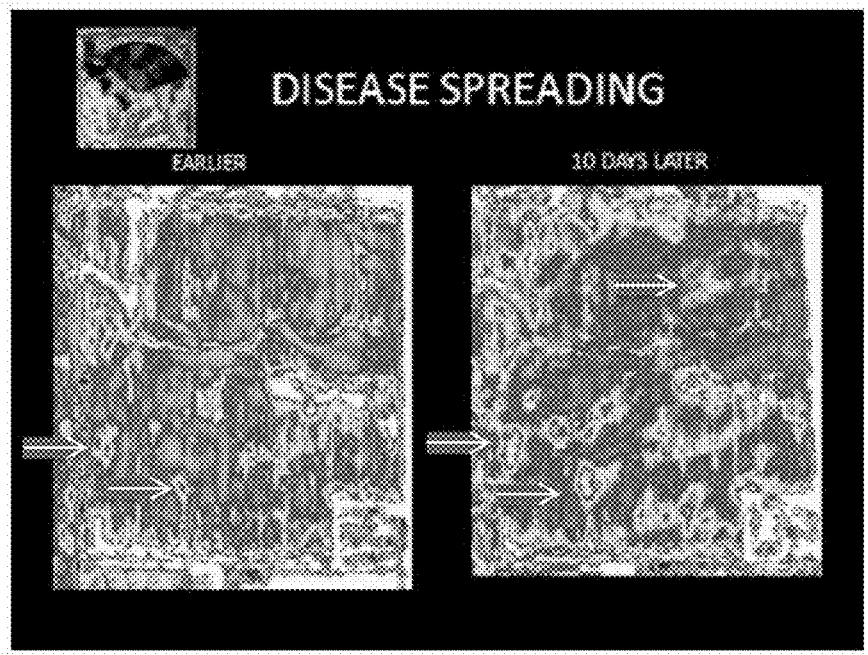
FIG. 7 represents a first thermal image (left) and a second thermal image (right) illustrating the spread of disease in vegetation in a field. Portions of the field inflicted by disease are identified with arrows.

Monitoring the health and growth of the plants may be further improved by acquiring a plurality of thermal images over a period of time, for example acquiring at least one thermal image of a field every two weeks during a growing season. Preferably, a computer program may then analyze or overlay multiple thermal images of a single field to assign a value to each pixel in the images. Patterns of disease or insect infestation may then be recognized and assessed. For example, disease may be spreading among the plants if the sizes of the patterns are increasing, or the plants may be recovering if the sizes of the patterns are decreasing. Preferably, the computer program applies a color palette to bring the identified pattern to the attention of an observer such as the farmer or agronomist. FIG. 7 represents a first thermal image (left) and a second thermal image (right). The second thermal image was taken ten days after the first thermal image and represents increases in three different diseased areas in an imaged field, each area indicated with an arrow.

In investigations leading to the present invention, it was determined that the difference in temperature (delta) between a lowest temperature of the plants in a given field and a highest temperature of the plants in the same field correlates directly with a yield potential of that field. For example, in low yield years the delta in temperature has been found to be fairly large due to the drastic contrast between the damaged plants and the plants in less affected areas of the field. In contrast, in high yield years where there has been less stress on the plants, the delta has been observed to be generally much smaller. In view of these findings, the software preferably may be used to analyze the thermal image and perform a yield prediction for at least part of a field based on variations in temperature, optionally along with farmer comments and/or other variables. According to one aspect of the invention, the software may provide a yield estimating tool that uses the thermal imagery to assign each pixel of a thermal image within a field boundary a yield prediction based on temperature, and user input at designated check points. For example, a farmer may physically perform yield checks at three locations in the field corresponding to three pixels on the thermal image having a coolest temperature, a warmest temperature, and a temperature therebetween and possibly midway between the coolest and warmest temperatures, and the software may then compare this information to the rest of the pixels in the field to perform a yield prediction of the entire field by comparing the pixels at the checked locations to other pixels in the thermal image. Since the yield prediction is based on each individual pixel in the captured thermal image, the prediction can be substantially more accurate than conventional yield estimate methods such as counting the yield in a random area of the field and then extrapolating this count to predict a yield of the entire field. In particular, yield predictions according to aspects of the present invention preferably take into account diseased areas of the field and the size of the produce grown. For example, when predicting the yield of a corn field, the yield prediction algorithm preferably takes into account the health of the plants, the size of the ears of corn that may be produced on the plants, the number of kernels on each ear of corn, and other specific information relative to each pixel in the thermal image which may not normally be accounted for in conventional predictions. Although the above nonlimiting process requires a field check of a minimum of three locations in the field in order to predict yield, additional locations may be field checked in order to potentially provide more accurate yield prediction results. Alternatively, it is foreseeable that the yield prediction may be calculated based solely on the difference in temperature between the warmest plants in the field and the coolest plants in the field, which may then be analyzed by the software in comparison to data accessible by the software, for example, known temperatures and yields of previous years and/or generic prediction algorithms of the software.

It is foreseeable and within the scope of the invention that the yield prediction process described herein may have broader applications than predicting the yield of a single field. In particular, a plurality of thermal images of a plurality of fields may be obtained and used to in aggregate to create a broad area yield index, representing a yield prediction for a geographic area corresponding to a region, state, country, or other relatively large coverage area. For example, a database may be created containing thermal images of fields across an entire country. The yield prediction process as previously described may be performed on each individual field. By combing the results of all of the fields in the database, an accurate national yield index may be calculated for the country. Alternatively, the national index may be produced by inspecting various points among the imaged fields to provide yield related data to the system. These points may then be compared to the rest of the pixels in the plurality of thermal images to calculate the yield prediction in the same manner as would be done for analyzing a single field. The thermal images used for determining the yield index may be filtered to provide indexes specific to individual crops, plants, or other parameters of interest. For example, the thermal images may be filtered such that only corn fields are represented which then provides a corn yield index for the coverage area. It is believed that yield indexes as described herein would be available sooner and are more accurate than conventional analyst publications, such as but not limited to the crop yield indexes published by the U.S. Department of Agriculture (USDA).

According to one aspect of the present invention, the digital visual image of the digital camera 14 may be analyzed and/or processed in order to render a hypersensitive "green filtered" image or Advanced Digital Vegetation Index (ADVI) image. For this purpose, the digital visual image preferably captures light in the near-infrared, visual, and ultraviolet spectrums. For this purpose, the digital camera 14 preferably captures as much of the light spectrum as possible. In investigations leading to aspects of the present invention, it was determined that by capturing images with commercially available high end digital cameras, and further using a computer algorithm to infer light intensity slightly beyond the range captured by the camera, it was possible to obtain a wavelength range suitable for producing the ADVI images. By using a combination of near-infrared light coupled with red absorption, green reflectance, and portions of the ultraviolet spectrum, the software may assign each pixel of the digital image an intensity value, for example, 1 to 255. The software may then apply a color palette to the image based on the pixel intensity values. The resulting ADVI image may represent differences in color across the crop canopy. FIG. 6 represents an aerial image of a field (left) and an ADVI image of the field (right) in accordance with an aspect of the invention. Such ADVI images may be analyzed in order to determine information such as but not limited to nitrogen loss in plants within a field. For example, by comparing an ADVI image and a thermal image of a field, a trained thermographer or computer software can determine if abnormalities to a group of plants are due to disease or lack of nutrients. This information may be used to build prescription maps for seed and fertilizer for individual fields, and to apply rescue treatments during the current season. These rescue treatments may include treating only the detrimentally effected plants in the field to address the disease or lack of nutrients. The imagery may also be used to plan or adjust the planting and fertilizing for the following season.

Although U.S. Pat. No. 7,058,197 discloses creating NDVI images based on light reflectance, only wavelengths in the visible spectrum between 0.38 to 0.72 micrometers are disclosed as being captured and analyzed. In contrast, the ADVI images disclosed herein are created by capturing digital images that capture as much of the light spectrum as possible, including near-infrared, visual, and portions of the ultraviolet spectrum and then applying computer algorithms to the digital images to determine the relative light reflectance between plants in the field. As such, the present ADVI images take into account substantial amounts of data which is believed to be excluded from the analysis performed in U.S. Pat. No. 7,058,197.

Figure 11:
FIG. 11 is an exemplary SSURGO map available from the U.S. Department of Agriculture (USDA).
Figure 12:
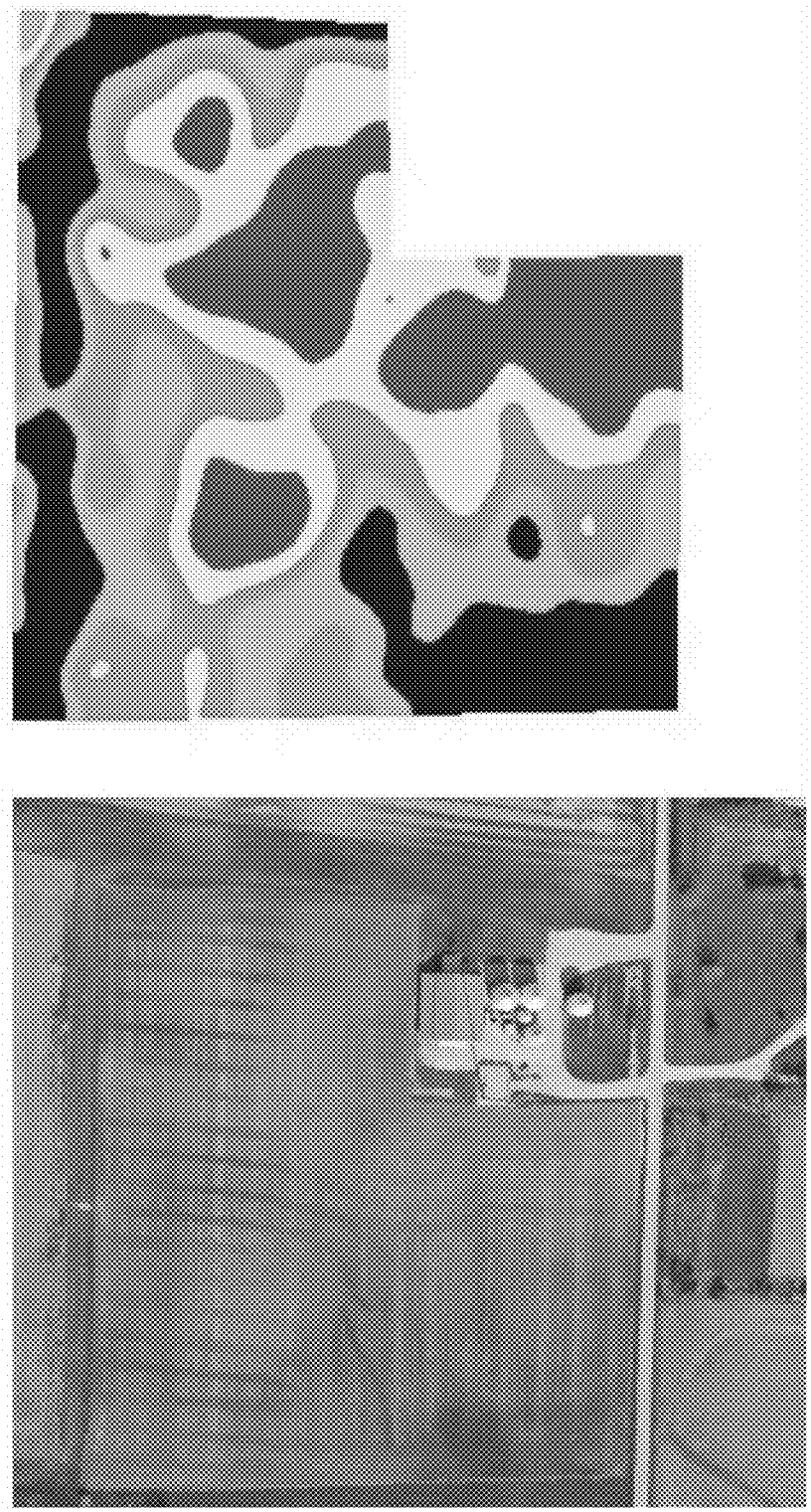
FIG. 12 includes a digital visual image and a thermal image of a bare field comprising little or no vegetation.

In addition to analyzing the health and nutrition of plants in a field, the ADVI images may be used to analyze bare fields prior to plants being planted in the field in order to determine the types of soil in the field. Such information can be beneficial for producing prescription maps. Conventionally, the soil type of a field is defined prior to determining an agricultural prescription. In the United States, this has historically been done using SSURGO (soil survey) maps that were originally generated by the USDA in the early 1970's. An exemplary SSURGO map is represented in FIG. 11. These maps are based on subjective observation by humans, and therefore may often be inconsistent and/or inaccurate. Because most farmers currently build their foundations for prescriptions from these maps, errors are inherently embedded in these foundations, and erroneous prescriptions are then generated. By utilizing a combination of the ADVI imagery in conjunction with thermal imagery as disclosed herein, it is possible to derive more accurate soil zones to use for these prescriptions. For example, both a visual digital image and a thermal image may be obtained of the bare soil (i.e., little or no vegetation) of a field. Exemplary images of a bare field are presented in FIG. 12 (visual image on left, thermal image on right). From the digital visual image, an ADVI image may be produce and then compared by the software or a trained thermographer to the thermal image to determine all of the various types of soil present in the field and their locations. Notably, the thermal image can be used to compensate for moisture in the field. For example, if only the ADVI image was analyzed without the use of the thermal image, wet areas of the field could be erroneously mistaken for areas of darker soil, because moisture can have the effect of reducing light reflectance. By comparing the ADVI image to the thermal image, it is possible to determine that a darker area of the field is merely wet, or relates to soil type that is darker than surrounding soil types. By analyzing the two types of images, a soil zone map may be produced accurately indicating boundaries or zones based on the colors captured within a field. As such, the software preferably includes a soil type difference indicator feature suitable for producing soil zone maps of fields based on the intensity of light reflected from the bare soil. Optionally, the software may allow a user the ability to choose how many zones the field is broken into (e.g., by adjusting the color range per zone). Soil zone maps produced in this manner will not comprise the errors believed to be inherent in prescription maps produced based on the subjective findings of humans such as the SSURGO maps.

Figure 13:
FIG. 13 is an image of a field representing the relative moisture throughout the field.

According to one aspect of the invention, a thermal image of a field obtained as described herein may be used in combination with other data-obtaining tools to provide additional information about the field. For example, the software may have an irrigation planning feature that works in combination with a soil moisture probe to calculate the moisture throughout an entire field, and may produce a moisture image representative of such moisture data. Currently, many farmers that utilize irrigation invest in at least one soil moisture probe for each of their fields. These probes and associated services are often very expensive. In addition, the probes are only capable of determining moisture content in the ground at the specific location where it is located, and not the moisture content of the rest of the field. According to a nonlimiting example, the GPS location of the single probe in the field can be overlaid on top of a thermal image of the field (i.e., assigned to a pixel in the thermal image corresponding to the location of the probe), and the software can then compare the relative temperatures of the pixel corresponding to the probe's location and other pixels in the thermal image to determine the moisture content of each pixel in the field. Effectively, this process multiplies the probe by millions across the entire field. In particular, the relativity among the pixels in the thermal image can be used to determine areas of the field that are wetter (cooler) than the location of the probe, and areas that are dryer (hotter). Based on this moisture information, the software or a user may determine the moisture content at any location within the field and how much, if any, water to apply to various sections of the field. Such information could further be uploaded into an irrigation controller, such that water may be automatically and selectively applied or not to various sections of the field depending on the real time requirements of each section. An irrigation system utilizing this data is believed to provide both economic as well as environmental benefits due to improved utilization of water. FIG. 13 represents a moisture image representative of moisture in a field. Circular moisture regions are represented that were formed due to the extents of an irrigation system operating in the field. Light colored rings can be seen within the circular areas representing warmer areas caused, in this instance, by nozzles on the irrigation system that were plugged and therefore not applying as much water.

Certain aspects of the invention encompass various modifications and improvements to the system described above, including but not limited to assisting ground inspection of the fields. For example, FIG. 1 schematically represents the use of a tracking device 22, such as a G.P.S. (Global Positioning System) device, located within or on the aircraft 10 to log the position of the aircraft 10 on timed intervals, such as once per second, in addition to storing the compass heading of the aircraft 10. Alternatively, the position and heading of the aircraft 10 may be logged by a system when an image is acquired by any of the imaging devices on the aircraft, such as the thermal imaging camera 12 or digital camera 14. Computer software can then be used to synchronize this information with the time at which each individual image is taken. The software may then rotate and orient all of the images in, for example, a "north up" orientation for easier referencing during ground inspection regardless of the flight path of the aircraft 10. For example, if a thermal image is acquired while the aircraft 10 is flying south, the thermal image will inherently represent the southern portion of the field near the uppermost portion of the image, that is, in a "south up" orientation. The software can utilize the logged position and heading of the aircraft 10 to rotate the image such that the northern portion of the field is in the uppermost portion of the image, that is, a "north up" orientation.

Figure 2:
FIG. 2 is a screen shot of a computer software interface providing access to a database of images sorted for an individual farm in accordance with an aspect of the present invention.

The information recorded by the tracking device 22 may further be used with computer software to geo-locate (georeference) all of the images (e.g., thermal images, visual digital images, ADVI images, soil zone maps, moisture images, etc.) and sort them into groups for each individual tract of land, for example a farm. Preferably, the software maps the images by superimposing each image on a geographical map at the corresponding location where the image was taken. In addition to improving ground inspections, this data may be used to compile a database of images sorted according to each individual farm, for example, as represented in FIG. 2. Preferably, the database comprises names for the fields and their corresponding coordinates. This allows the software to not only superimpose the image on a geographical map at its corresponding location but also to provide the name of the field captured in the image. For example, the image may be superimposed on a geographical map with a digital tag or label comprising the name of the client, farm, and/or specific field represented in the image. For larger databases, the image may be labeled to comprise additional information, such as a name of a company that owns, leases, or is otherwise related to the farm, a division within the company, an agronomist, the client, farm, specific field, or other relevant information. Preferably, the software provides tools for modifying the images, correcting for camera errors, comparing and magnifying images, exporting images to various file formats, adding and saving user or system generated comments to the images, and notifying the companies, clients, etc., via email, mobile texting, or the like of changes to their respective accounts, such as a new image being added to the database.

Ground inspections can further be improved by providing the user with access to a database of images as described herein during the physical ground inspection. This may be accomplished either by providing a georeferenced image to a handheld mobile device (for example, a tablet computer, cellular phone, laptop computer, or the like), or by georeferencing the image with such a mobile device using software written specifically for this purpose. Preferably, the software is adapted to automatically download each image associated with a particular parcel or client, for example using a File Transfer Protocol (FTP) method, and allow viewing of all the associated images. Alternatively, if the handheld device has wireless Internet capabilities, the software may be adapted to communicate remotely with the database, and allow viewing of the images without the need to download the images. The user can then choose to load any image to an overlay map and manually manipulate the image to align field boundaries.

Figure 3:
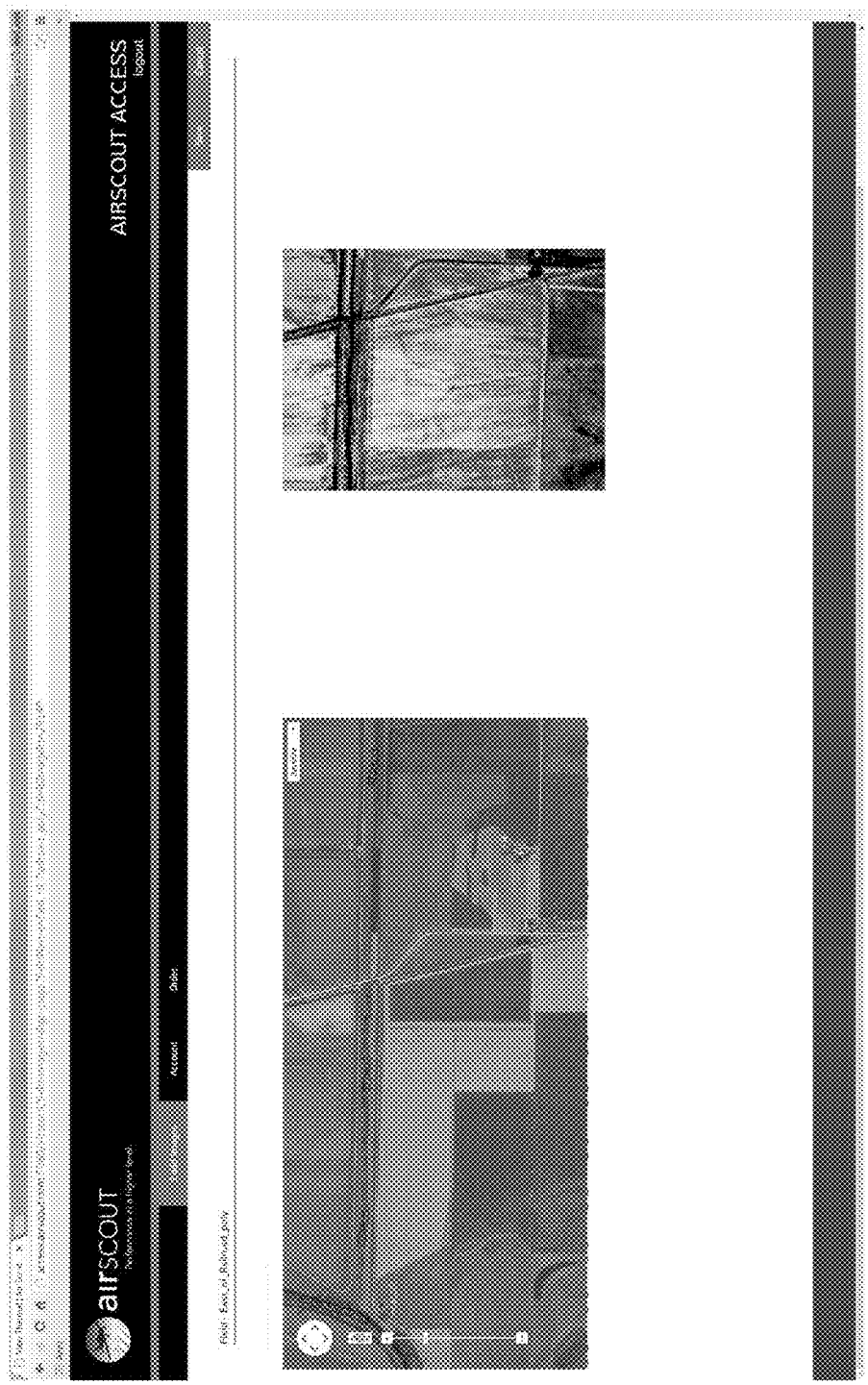
FIGS. 3-5 are screen shots of a computer software interface representing a process of aligning and superimposing a thermal image of a field on a digital image of the field to create an overlaid image that is mapped to a geographical map.
Figure 4:
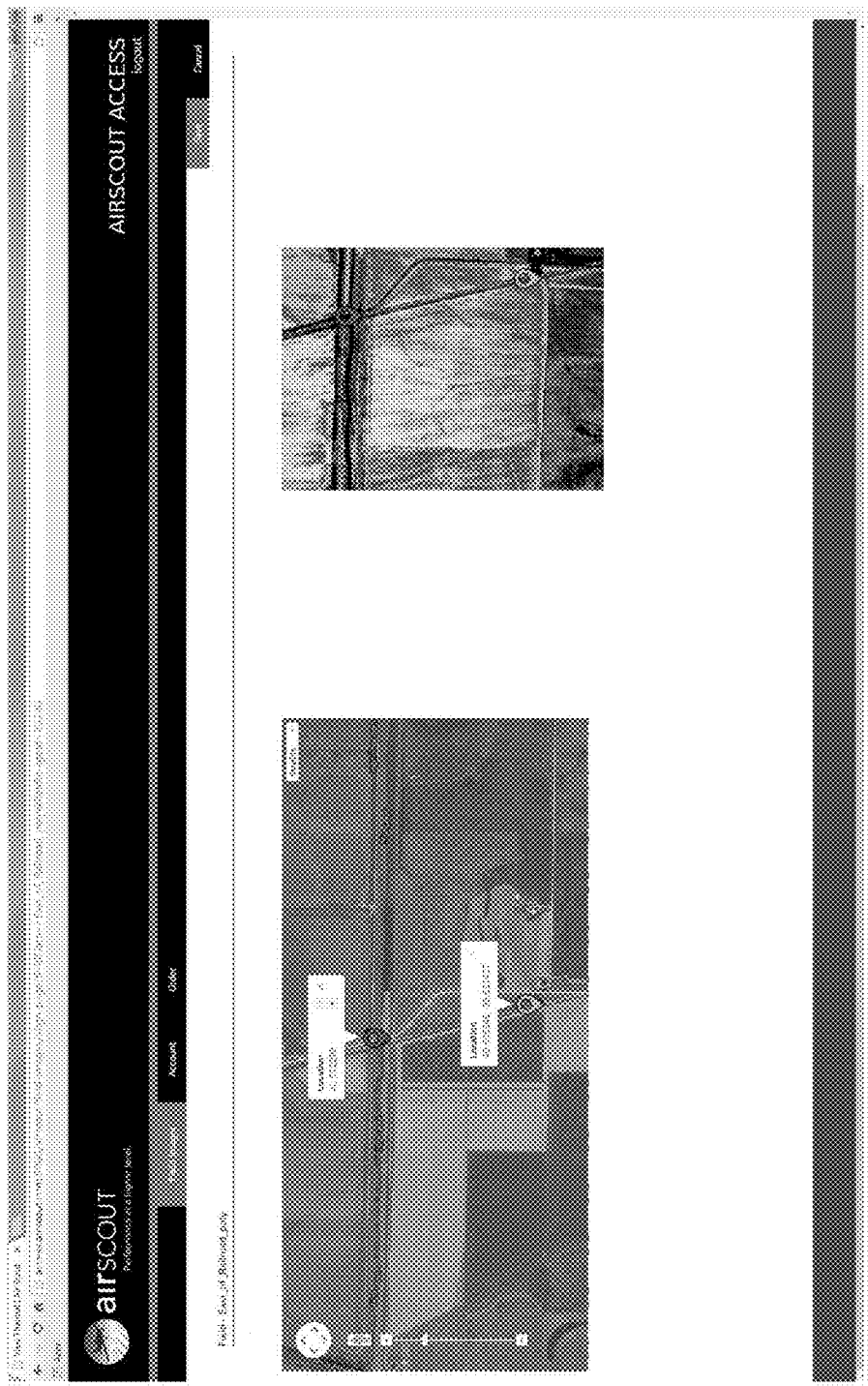
Figure 5:

According to one aspect of the invention, the software allows the user to choose two common points between the image and a map in order to georeference the images. For example, FIG. 3 represents a screenshot with a geographical map on the left and a thermal image of a field on the right. FIG. 4 represents two geographical points identified on both the geographical map and the thermal image by a user. FIG. 5 represents the thermal image overlaid on the geographical map based on the two common geographical points identified by the user in FIG. 4. Preferably, the software is adapted to allow the user to adjust the color tone and transparency of the image for viewing purposes, for example, to create a composite image comprising aspects of both the image (e.g., thermal image, visual digital image, ADVI image, soil zone map, moisture image, etc.) and the underlying map that are visible. The user can then walk through the field with the user's present location shown on top of the image, geographical map, or composite image, allowing the ability to precisely navigate to the areas of most interest. For this purpose, the handheld device preferably comprises G.P.S. tracking capabilities or other location sensing functionality. In the case of poor plant health, the user can then gather samples and determine the cause of the anomaly in question. If this invention is used for analyzing a farm, timeliness of the ground inspection of the plants is critical for the farmer to make important management decisions. Therefore, quick access to the images is a particularly advantageous aspect of the process and system.

Figure 14:
FIG. 14 is a screen shot of a computer software interface suitable for remotely inspecting a field with an unmanned aerial vehicle.

In addition to assisting in ground inspections as described previously, the system and/or images described herein may assist in remote inspection of a field. For example, it is within the scope of the invention that a field may be inspected remotely with an unmanned aerial vehicle (drone) or other small aircraft that may be remotely flown (manually or autonomously) over a field that has been imaged in accordance with embodiments of the present invention. In nonlimiting investigations leading to aspects of the present invention, a drone was modified such that all of its conventional controls were bypassed. A commercially available "smart" cellular phone was mounted to a bottom surface of the drone. While other functionally equivalent components could be used in place of the phone, it provided several notable functions such as but not limited to visual imaging with a camera, location tracking with a G.P.S. device, computing capabilities, and communication means through a cellular network. During operation, the drone flew over a field while the camera on the phone provided a live camera view of the field from the bottom of the drone to a user interface, in this instance a mobile app operating on a computer tablet. A user was able to observe a georeferenced aerial image (for example, a thermal image) of the field and indicate thereon locations in the field that the user desired to inspect. The user interface sent a signal comprising the locations to a server, which then sent the signal to the phone on the drone. The phone then controlled the drone to autonomously fly over the specified locations in the field. During flight, the phone was in constant communication with the user interface, providing the live camera view and location of the drone to the user interface. At any time during the flight, the user interface could be used to instruct the phone to capture still images of the field, particularly over the potentially afflicted areas indicated by the aerial image. The captured images were saved in full resolution and sent to a server for storage and further inspection. FIG. 14 represents a screen shot of a user interface for operating the drone. The interface includes a georeferenced thermal image (right) with a location 30 indicated (pinned) thereon, and a digital visual image (left) representing a contemporaneous view of the field from the drone as it flew over the field. The location of the drone at the time the digital visual image was acquired is indicated on the thermal image by a solid circle 32. A particularly useful benefit of using a smart cellular phone was the drone could be controlled through the cellular network, rather than relying on a Wi-Fi signal or other wireless means of communication that may have less coverage compared to commercial cellular networks.

Remote inspection methods such as the above example allows for a field to be remotely inspected by a trained agronomist without their actual physical presence being needed at or near the field. For example, the drone could be launched at the field remotely, autonomously, or by a person at the field. A trained agronomist may then take control of the drone and perform an inspection of the field remotely, regardless of the location of the agronomist. This would allow the trained agronomist to remotely inspect fields around the world from a single location.

The importance of the technology provided by the present invention cannot be overstated due to recent developments in agricultural practices. Chemical supply companies have released fungicide products onto the market to combat many diseases of nearly all commercially grown crops. These fungicides have proven to provide such an economic advantage that many farmers have preemptively contracted this service to be sprayed from airplanes using a "blanket coverage" technique, and therefore even in areas where disease is not present. Though this may be considered a preventative measure and potentially beneficial, in many instances it may not. With the process of the present invention, crop health can be monitored to enable a farmer to react in sufficient time to mitigate damage in the event that a crop becomes infested. This is enormously beneficial from an economic standpoint, and quite possibly from an environmental standpoint. In addition to monitoring plant health, the thermal images may be used to determine other vital statistics regarding the plants. For example, the thermal images may be analyzed in order to inform the farmer of a predicted yield of a crop over an entire farm or for portions of a single field and/or to identify nitrogen loss in a crop.

Though U.S. Pat. No. 7,058,197 broaches certain topics of interest to the present invention, the method and system described herein rely on wavelengths in the range of about 7 to 14 micrometers, which is a different region of the electromagnetic spectrum. U.S. Pat. No. 7,058,197 appears to make an assumption that moisture is the primary mechanism affecting reflectance, more specifically, higher moisture contents correspond to lower reflectance. Though not wishing to be held to any particular theory, the present invention recognizes the significance of radiated energy, in other words, warmer surfaces emit more energy, and that moisture is simply a medium that promotes energy absorption as opposed to energy emittance. It also appears to be evident that U.S. Pat. No. 7,058,197 relies on reflected light energy, whereas the process and system of the present invention do not require light, but simply measure infrared radiation from the target body.

The process of the present invention also does not require a calibration procedure of the type required by U.S. Pat. No. 6,597,991, and is more driven by relativity. Therefore, ground-based measurements are not required for the present invention.

While the invention has been described in terms of particular equipment and technologies, it is apparent that other forms could be adopted by one skilled in the art. For example, improved technologies could provide greater resolution of the thermographic image. Furthermore, it is foreseeable that infrared images could be acquired with satellite cameras, though as yet resolution is believed to be inadequate for use with the present invention due to atmospheric attenuation. Therefore, the scope of the invention is to be limited only by the following claims.

The invention claimed is:

1. A method of analyzing a field, the method comprising:
positioning an imaging system in an aircraft;
acquiring with the imaging system an aerial thermal image and an aerial digital visual image of at least a portion of the field that contains plants while the aircraft is in flight over the field, wherein the aerial thermal image comprises pixels indicating different levels of thermal energy emitted by the plants within the portion of the field while the aircraft is in flight over the field, and the aerial digital visual image comprises pixels indicating different levels of light reflected by the portion of the field while the aircraft is in flight over the field;
identifying at least three of the pixels on the aerial thermal image, a first of the pixels indicating a lowest temperature in the aerial thermal image, a second of the pixels indicating a highest temperature in the aerial thermal image, and a third of the pixels indicating a temperature between the lowest and highest temperatures of the first and second pixels;

processing the aerial thermal image to assess relative variations in temperatures among the plants within the portion of the field by assessing variations in the pixels of the aerial thermal image, determining a temperature difference between the lowest and highest temperatures of the plants, and comparing the temperature difference and the first, second, and third pixels to each of the pixels in the aerial thermal image to assign each of the pixels thereof with a yield prediction based on temperature to perform a yield prediction of the plants in the portion of the field; and comparing the aerial digital visual image to the aerial thermal image.

2. The method of claim 1, further comprising:
georeferencing the aerial thermal image by superimposing the aerial thermal image on a geographical map of the field to obtain a georeferenced aerial thermal image;
providing the georeferenced aerial thermal image to a handheld device located in the field; and
locating and displaying the present position of the handheld device on the georeferenced aerial thermal image.

3. The method of claim 1, further comprising:
georeferencing the aerial thermal image by superimposing the aerial thermal image on a geographical map of the field to obtain a georeferenced aerial thermal image;
providing the georeferenced aerial thermal image to a user interface;
indicating with the user interface a location on the georeferenced aerial thermal image to be inspected in the field;
operating an unmanned aerial vehicle to fly over the location in the field, the unmanned aerial vehicle having a camera; and
controlling the unmanned aerial vehicle with the user interface to fly over the location in the field while providing to the user interface a live camera view of the field with the camera and an indication on the georeferenced aerial thermal image of where the unmanned aerial vehicle is over the field as the live camera view is acquired.

4. The method of claim 1, wherein the aerial thermal image is a first aerial thermal image, the method further comprising:
acquiring a second aerial thermal image of the portion of the field that is indicative of the thermal energy emitted by the plants within the portion of the field while the aircraft is in flight over the field at a time after the first aerial thermal image is acquired;
processing the second aerial thermal image to assess variations in temperatures among the plants; and
comparing the first aerial thermal image with the second aerial thermal image to assess the health or growth of the plants over a time period between when the first aerial thermal image was acquired and the time when the second aerial thermal image was acquired.

5. The method of claim 1, wherein the variations in temperatures among the plants are assessed to detect disease in the plants.

6. The method of claim 1, wherein the variations in temperatures among the plants are assessed to detect insect infestation in the plants.

7. The method of claim 1, wherein the portion of the field further comprises bare soil having substantially no vegetation, the aerial thermal image is indicative of thermal energy emitted by the bare soil within the portion of the field while the aircraft is in flight over the field, the aerial digital visual image is indicative of the light reflected by the bare soil within the portion of the field while the aircraft is in flight over the field, and the processing of the aerial thermal image assesses the relative variations in the temperatures of the bare soil, the method further comprising:
processing the aerial digital visual image to assess relative variations in light reflectance of near-infrared, visible, and ultraviolet spectrums of the light in the aerial digital visual image and assign an intensity value to each of the pixels of the aerial digital visual image across the field; and
analyzing the relative variations in the temperatures across the field and the relative variations in the light reflectance across the field to identify soil types within the portion of the field.

8. The method of claim 1, wherein the aerial digital visual image is indicative of light reflected by the plants within the portion of the field while the aircraft is in flight over the field, the aerial digital visual image captures light in near-infrared, visible, and ultraviolet spectrums, and the method further comprises processing the aerial digital visual image to assess relative variations in the near-infrared, visible, and ultraviolet spectrums of light reflectance among the plants.

9. The method of claim 8, the method further comprising:
comparing the relative variations in the near-infrared, visible, and ultraviolet spectrums of the light reflectance among the plants and the relative variations in the temperatures among the plants to assess stress factors among the plants.

10. A method of analyzing a field, the method comprising:
positioning an imaging system in an aircraft;
acquiring with the imaging system an aerial thermal image and an aerial digital visual image of at least a portion of the field while the aircraft is in flight over the field, wherein the aerial thermal image comprises pixels indicating different levels of thermal energy emitted within the portion of the field while the aircraft is in flight over the field, and the aerial digital visual image comprises pixels indicating different levels of light reflected by the portion of the field while the aircraft is in flight over the field;
processing the aerial thermal image to assess relative variations in temperatures within the portion of the field by assessing variations in the pixels of the aerial thermal image;
comparing the aerial digital visual image to the aerial thermal image;
locating a soil moisture probe at a location within the portion of the field;
sensing a moisture content at the location with the soil moisture probe;
identifying the location of the soil moisture probe on the aerial thermal image;
assigning the location of the soil probe to one of the pixels of the aerial thermal image;
comparing a temperature associated with the one pixel to temperatures of others of the pixels in the aerial thermal image to assign each of the others of the pixels with a moisture content relative to the moisture content sensed by the soil moisture probe at the location assigned to the one pixel; and
determining moisture content across the field based on the moisture content sensed by the soil moisture probe and the moisture contents assigned to the others of the pixels.

11. A system for analyzing a field, the system comprising:
an imaging system in an aircraft, the imaging system being operable to acquire an aerial thermal image and an aerial digital visual image of at least a portion of the field that contains plants while the aircraft is in flight over the field, wherein the aerial thermal image comprises pixels indicating different levels of thermal energy emitted by the plants within the portion of the field while the aircraft is in flight over the field, and the aerial digital visual image comprises pixels indicating different levels of light reflected by the portion of the field while the aircraft is in flight over the field;
means for identifying at least three of the pixels on the aerial thermal image, a first of the pixels indicating a lowest temperature in the aerial thermal image, a second of the pixels indicating a highest temperature in the aerial thermal image, and a third of the pixels indicating a temperature between the lowest and highest temperatures of the first and second pixels;
means for processing the aerial thermal image to assess relative variations in temperatures among the plants within the portion of the field by assessing variations in the pixels of the aerial thermal image, determining a temperature difference between the lowest and highest temperatures of the plants, comparing the temperature difference and the first, second, and third pixels to each of the pixels in the aerial thermal image to assign each of the pixels thereof with a yield prediction based on temperature to perform a yield prediction of the plants in the portion of the field, and comparing the aerial digital visual image to the aerial thermal image.

12. The system of claim 11, further comprising:
means for georeferencing the aerial thermal image by superimposing the aerial thermal image on a geographical map of the field to obtain a georeferenced aerial thermal image;
means for overlaying the aerial image on the geographical map;
means for providing the aerial image on the geographical map to a handheld device located in the field and having means for locating and displaying the present position of the handheld device on the georeferenced aerial thermal image.

13. The system of claim 11, further comprising:
means for georeferencing the aerial thermal image by superimposing the aerial thermal image on a geographical map of the field to obtain a georeferenced aerial thermal image;
means for overlaying the aerial image on the geographical map;
an unmanned aerial vehicle having a camera for providing a live camera view of the field;
a user interface having means for displaying the georeferenced aerial thermal image, means for indicating the location to be inspected on the georeferenced aerial thermal image, means for controlling the unmanned aerial vehicle to fly over the location in the field while providing to the user interface the live camera view of the field and an indication on the georeferenced aerial thermal image of where the unmanned aerial vehicle is over the field as the live camera view is acquired.

14. The system of claim 11, wherein the aerial thermal image is a first aerial thermal image, the system further comprising:
means for acquiring a second aerial thermal image of the portion of the field that is indicative of the thermal energy emitted by the plants within the portion of the field while the aircraft is in flight over the field at a time after the first aerial thermal image is acquired;
means for processing the second aerial thermal image to assess variations in temperatures among the plants; and
means for comparing the first aerial thermal image with the second aerial thermal image to assess the health or growth of the plants over a time period between when the first aerial thermal image was acquired and the time when the second aerial thermal image was acquired.

15. The system of claim 11, wherein the variations in temperatures among the plants are assessed to detect disease in the plants.

16. The system of claim 11, wherein the variations in temperatures among the plants are assessed to detect insect infestation in the plants.

17. The system of claim 11, further comprising:
a soil moisture probe at a location within the portion of the field corresponding to a location on the aerial thermal image and assigned to one of the pixels of the aerial thermal image, the soil moisture probe sensing a moisture content at the location; and
software that compares a temperature associated with the one pixel to temperatures of others of the pixels in the thermal image to assign each of the others of the pixels with a moisture content relative to the moisture content sensed by the soil moisture probe at the location assigned to the one pixel, and determines moisture content across the field based on the moisture content sensed by the soil moisture probe and the moisture contents assigned to the others of the pixels.

18. The system of claim 11, wherein the portion of the field further comprises bare soil having substantially no vegetation, the aerial thermal image is indicative of thermal energy emitted by the bare soil within the portion of the field while the aircraft is in flight over the field, the aerial digital visual image is indicative of the light reflected by the bare soil within the portion of the field while the aircraft is in flight over the field, and the means for processing the aerial thermal image assesses the relative variations in the temperatures of the bare soil, the system further comprising:
means for processing the aerial digital visual image to assess relative variations in light reflectance of near-infrared, visible, and ultraviolet spectrums of the light in the aerial digital visual image and assign an intensity value to each of the pixels of the aerial digital visual image across the field; and
means for analyzing the relative variations in the temperatures across the field and the relative variations in the light reflectance across the field to identify soil types within the portion of the field.

19. The system of claim 11, wherein the aerial digital visual image is indicative of light reflected by the plants within the portion of the field while the aircraft is in flight over the field, the aerial digital visual image captures light in near-infrared, visible, and ultraviolet spectrums, and the system further comprises means for processing the aerial digital visual image to assess relative variations in the near-infrared, visible, and ultraviolet spectrums of light reflectance among the plants.

20. The system of claim 19, the system further comprising:
means for comparing the relative variations in the near-infrared, visible, and ultraviolet spectrums of the light reflectance among the plants and the relative variations in the temperatures among the plants to assess stress factors among the plants.

* * * * *